United States Patent

Hickey et al.

[11] Patent Number: 5,085,831
[45] Date of Patent: Feb. 4, 1992

[54] APPARATUS FOR CONTINUALLY AND AUTOMATICALLY MEASURING THE LEVEL OF A WATER TREATMENT PRODUCT IN BOILER FEEDWATER

[75] Inventors: James J. Hickey, Palos Heights, Ill.; William L. Adamson, Olympia, Wash.

[73] Assignee: Nalco Chemical Company, Naperville, Ill.

[21] Appl. No.: 670,491

[22] Filed: Mar. 15, 1991

Related U.S. Application Data

[63] Continuation of Ser. No. 422,566, Oct. 17, 1989, abandoned.

[51] Int. Cl.⁵ .............................................. G01N 21/83
[52] U.S. Cl. .......................................... 422/62; 422/82; 422/82.05; 422/82.09; 356/246; 356/247
[58] Field of Search ............................. 356/246, 247; 422/82.05, 82.09, 82, 62

[56] References Cited

U.S. PATENT DOCUMENTS

| | | | |
|---|---|---|---|
| 3,895,913 | 7/1975 | Bockowski et al. | 23/230 R |
| 3,953,136 | 4/1976 | Hach | 356/181 |
| 4,457,847 | 7/1984 | Lorenc et al. | 210/698 |
| 4,715,710 | 12/1987 | Andersen | 356/246 |

OTHER PUBLICATIONS

"Determination of Polyacrylamides", W. B. Crummett & R. A. Hummel, Journal AWWA, Feb., 1963, pp. 211-219.
"Products for Process Analysis", Hach Company, Mar. 1989.

Primary Examiner—David L. Lacey
Assistant Examiner—David Redding
Attorney, Agent, or Firm—Lloyd L. Zickert

[57] ABSTRACT

An apparatus to continuously measure the level of a water treatment product added to boiler feedwater for prevention of scale formation in boiler tubes, which includes a pump turbidimeter analyzer receiving a sample of the treated boiler feedwater and mixing it with a reagent to produce turbidity in the sample that is photometrically measured to determine product level.

5 Claims, 2 Drawing Sheets

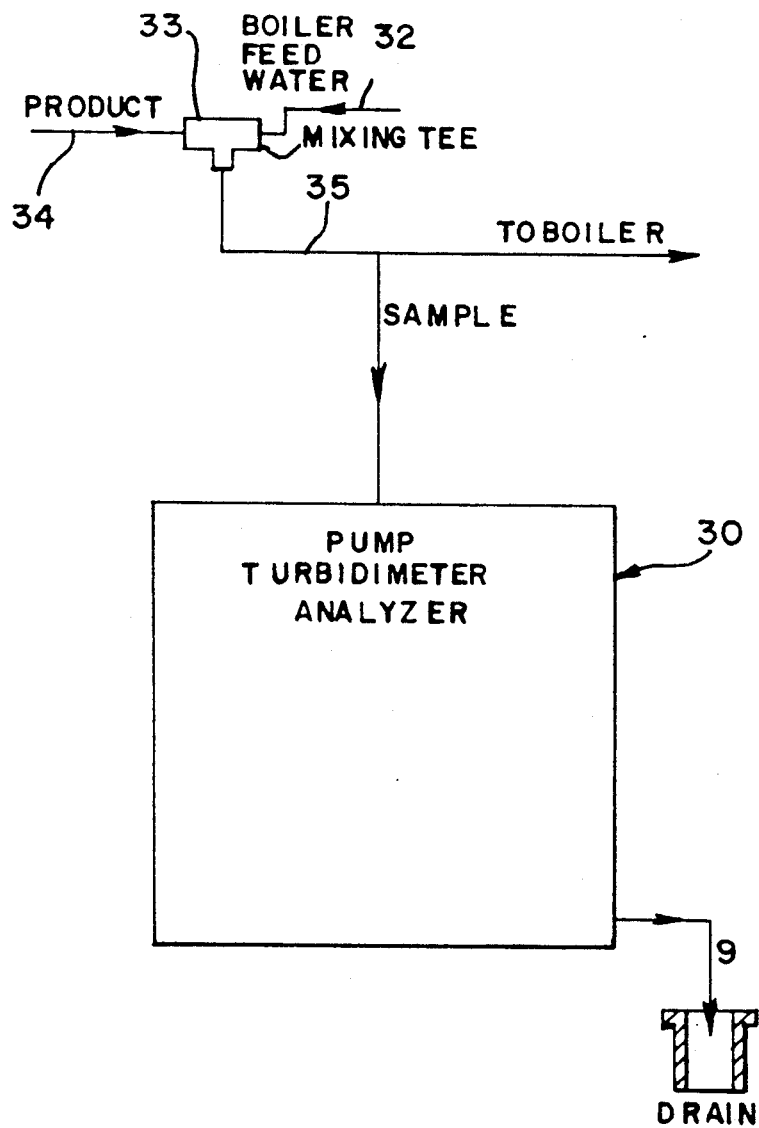

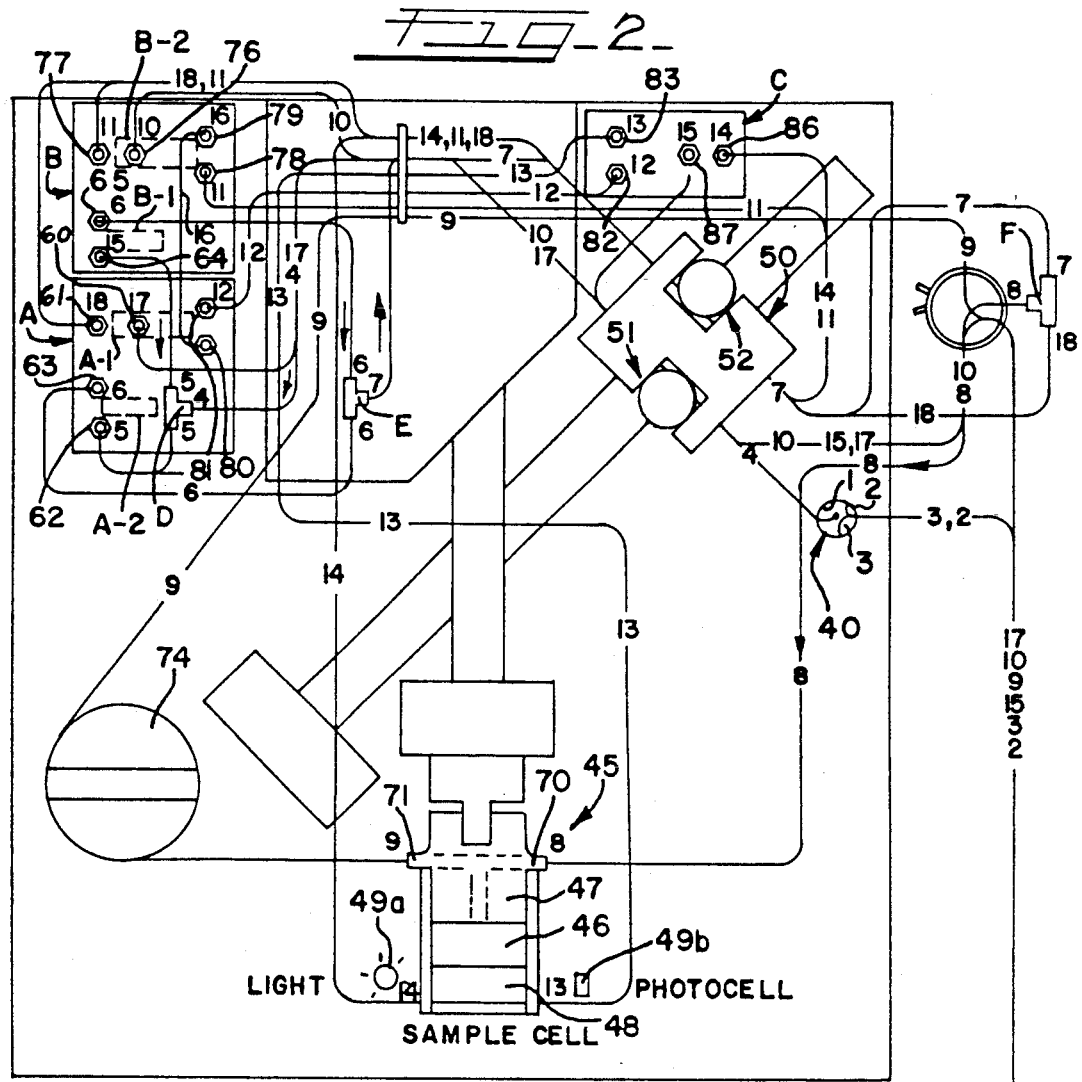
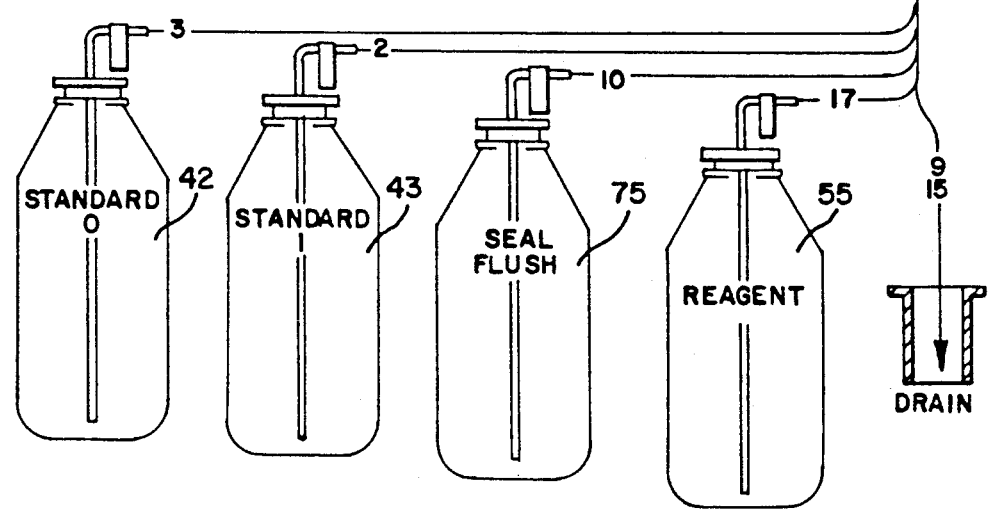

APPARATUS FOR CONTINUALLY AND AUTOMATICALLY MEASURING THE LEVEL OF A WATER TREATMENT PRODUCT IN BOILER FEEDWATER

This application is a continuation of application Ser. No. 422,566, filed Oct. 17, 1989, now abandoned.

DESCRIPTION

This invention relates in general to an apparatus for continuously and automatically measuring the level of a treatment chemical in boiler feedwater where the chemical has been added to provide scale prevention without corrosion potential.

BACKGROUND OF THE INVENTION

It is well known to add chelating agents to boiler water for the purpose of preventing scale formation on the internal surfaces of boiler tubes caused by hardness deposits. However, such agents are known to cause undesirable corrosion under certain conditions.

It has also been known to photometrically determine chelant level in industrial water by adding a second chelating agent and a color indicator to a water sample for photometrically making absorbance readings and comparing the absorbance value to a predetermined set of absorbance values plotted against ppm levels of chelant excesses or deficiencies.

It has also been known to treat industrial water and particularly boiler water with a product that includes a copolymer of acrylamide and acrylate and a copolymer of acrylic acid and sodium vinyl sulphonate which is sold by Nalco Chemical Company of Naperville, Illinois, under the trademark "TRANSPORT PLUS" such as Nalco 7200 and as disclosed in their U.S. Patent No. 4,457,847. It has also been known to manually test the level of such a polymer in the water by taking a sample, adding a reagent that will coact with only the acrylate component of the product and produce turbidity so that the reacting solution can be subjected to a photometric analysis. Such a test procedure depends completely upon the skill of the test operator.

With the increasing demand of industry for improved reliability and control, there is a need for automating testing procedures, and particularly with respect to determining the level of a water treatment product in boiler feedwater.

It has further been known to provide test equipment such as the pump colorimeter analyzers sold by the Hach Company of Loveland, Colorado. Other analyzers have also been made for measuring turbidity in solutions. However, no analyzer has been available for continually testing boiler feedwater for the level of a water treatment product of the type in the above patent.

SUMMARY OF THE INVENTION

The present invention overcomes the heretofore encountered difficulties of providing reliable testing of product level in being able to continually and automatically monitor or measure the level of a water treatment product, of the type referred to above, in boiler feedwater by providing a new and unique automatic and continuous test method, and an analyzer capable of mixing a sample of the feedwater having the product with a reagent capable of producing a turbidity in the sample as a measure of product level that can be photometrically measured so as to determine the level of the product in parts per million (ppm) in the feedwater. The product includes a copolymer of acrylamide and acrylate and a copolymer of acrylic acid and sodium vinyl sulphonate. The reagent is formulated to chemically react with the total acrylate component, the acrylate and the acrylic acid, of the product to develop a turbidity in the reacted sample which when measured can be translated into the level of product in the feedwater.

The apparatus for analyzing the sample includes a mixing device for mixing the sample with a reagent capable of reacting with the total acrylate component of the product so as to develop turbidity in the reacted sample that can be photometrically measured to determine the level of the product in the feedwater. The solution to be measured which includes the mixture of the sample and the reagent is pumped through a tubing system in precise proportions by use of metering pumps, and under the directional control of a pinch valve mechanism, to a photometer having an inlet and an outlet to a measuring cell, wherein the sample measured is controlled by a two-stroke pump. During the intake stroke a charge of new solution with a charge of the old solution is mixed in the cell for photometric measurement of the turbidity, and during the discharge stroke the mixed solution is discharged into a discharge line which is arranged so that on the intake stroke a part of the sample just analyzed photometrically is returned to the cell and mixed with a charge of new sample for the next analysis. This particular testing involves the use of a sufficient volume to accommodate a larger photocell for increased sensitivity.

By continually analyzing the level of the product, proper control of the product in proportion to the hardness ratio of the feedwater can be maintained to properly control deposits and corrosion and maintain optimum and efficient operation. Minimization of deposits maintains the tubes in optimum operating condition, thereby automatically reducing downtime of the boiler for cleaning the tubes. Further, by properly maintaining the level of the product to treat the boiler feedwater for optimum efficiency will maximize cost efficient operation.

It is therefore an object of the present invention to provide a new and improved method and apparatus for continually and automatically measuring the level of a water treatment product in boiler feedwater to automate the test procedure and eliminate the dependence on operator skill, thereby enhancing improved reliability and control of boiler operation.

Other objects, features and advantages of the invention will be apparent from the following detailed disclosure, taken in conjunction with the accompanying sheets of drawings, wherein like reference numerals refer to like parts.

DESCRIPTION OF THE DRAWINGS

FIG. 1 is a block schematic diagram illustrating the taking of a sample of product treated boiler feedwater and feeding it to a pump turbidimeter analyzer according to the present invention; and FIG. 2 is a schematic diagram of the analyzer according to the present invention.

DESCRIPTION OF THE INVENTION

The present invention is to a method and apparatus for continuously and automatically measuring the level of a water treatment chemical product that has been added to boiler feedwater for controlling hardness to prevent scale formation on heat transfer surfaces. Depending upon hardness, the level of product is proportioned so as to provide the optimum treatment and obtain optimum performance. The improved method of the invention measures the product level reliably to determine on a continuous and automatic basis whether the product to be added should be increased or decreased so as to provide optimum operation in reducing scale formation and/or removing scale without introducing a potential for corrosion.

The water treatment product providing scale prevention control for which the level is determined is a copolymer of acrylamide and acrylate and a copolymer of acrylic acid and sodium vinyl sulphonate made and sold by Nalco Chemical Company under the trademark "TRANSPORT PLUS".

The method includes the steps of metering precise volumes of a sample and a reagent, and mixing the sample and reagent to produce a turbidity in the sample as a level of ppm product, and photometrically measuring the sample to readout the level of product in the feedwater. The reagent is formulated to coact only with the total acrylate component of the product. Mixing of the sample and reagent defines a reacted sample which is charged in a predetermined amount into a measuring cell where it can be subjected to a photometric analysis to measure the turbidity. The sample in the cell that is measured constitutes a part of the new sample prepared and a part of the previously measured sample.

The apparatus comprises an analyzer which includes a selector valve for selecting solutions for calibrating the apparatus or for selecting the sample taken from the boiler feedwater line to test the sample. The analyzer mixes the sample with a turbidity developing reagent and photometrically measures in a measuring cell the turbidity formed in the reacted sample to determine the level of the water treatment product. The apparatus further includes pumps for precisely metering amounts of the sample and reagent to be mixed and delivered to the measuring cell. A pinch valve mechanism controls the direction of flow of the sample and reagent through the analyzer until they are mixed to form a reacted sample which is then delivered to the measuring cell. The measuring cell is precisely dimensioned and is loaded and discharged by a piston with seals in a cylinder and the seals are lubricated or flushed to maintain the cell clean from contaminants. The readout of the analyzer is an analog instrument or meter which is calibrated and reads out ppm of product which is indicative of the product level in the boiler system.

Referring now to the drawings and particularly to FIG. 1, a schematic diagram illustrates the manner of taking a sample to the analyzer which is defined as a pump turbidimeter analyzer and generally designated by the numeral 30. The sample enters the analyzer as 1 through a line and following measurement of the product level in the photometer is discharged from the analyzer to drain through a line as 9. Boiler feedwater is delivered through line 32 to a mixing tee or mixing device 33. The water treatment product is added in a precise amount depending upon the hardness of the boiler feedwater through product inlet line 34. The resulting treated boiler feedwater is then delivered from the mixing tee to the boiler through the boiler feedwater line 35. The sample is taken from the boiler feedwater line 35 as 1 to the analyzer. A schematic diagram of the analyzer 30 is shown in FIG. 2. The sample 1 comes into a three-way selector valve 40 which also has inlets for receiving lines 2 and 3 connected to calibration solution containers 42 and 43 respectively that are utilized for calibrating the analyzer. Calibration using standard 0 and standard 1 reference solutions is carried out in a well known fashion to establish reference points and calibrate the analog readout meter.

The analyzer further includes a photometer 45, metering pumps A, B and C, a pinch valve mechanism 50, a splitting tee D, a combining tee E, and a mixing tee F, all interconnected by lines as set forth herein relative to the flow pattern.

The photometer 45 measures turbidity which is caused by the presence of suspended particles in the sample to be measured and translates it to ppm (parts per million) of water treatment product in the sample.

In order to produce the turbidity in the sample, a specially formulated reagent is mixed with the product which combines with the total acrylate component of the product which includes the acrylate and the acrylic acid. The formulation and makeup procedure for this reagent is as follows:

MATERIALS

| Sodium Citrate, reagent grade | 50 grams |
| Sodium Hydroxide, reagent grade | 15 grams |
| Ethylene Diamine Tetraacetic Acid, disodium salt (EDTA-Na$_2$) | 93 grams |
| Monoethanolamine | 10 milliliters |
| Hydrochloric Acid, reagent grade | 6 milliliters |
| Distilled Water Q/S | 1 liter |
| Benzethonium Chloride (Hyamine 1622 by Rohm & Haas) | 5.0 grams |
| Ethoxylatede Nonyl Phenol (Triton N-101 by Rohm & Haas) | 2.0 grams |

PREPARATION

1. Add 50 grams of sodium citrate to 800 milliliters of distilled water. Mix to dissolve.
2. Add 15 grams of sodium hydroxide, dissolve.
3. Add 93 grams of EDTA-Na$_2$, dissolve.
4. Add 10 milliliters of monoethanolamine, mix.
5. Add 6 milliliters of hydrochloric acid, mix.
6. Dilute to 1 liter with distilled water and mix until homogeneous.
7. Solution pH should be adjusted to $10.8 \pm 0.3$ with monoethanolamine or hydrochloric acid.
8. Add 5.0 grams of Hyamine 1622, dissolve completely.
9. After Hyamine has dissolved, add 2.0 grams of Triton N-101.

The reagent supply is in container 55 and delivered to the analyzer by a reagent line as 17 through the lower part 51 of the pinch valve 50 to an inlet 60 of upper piston A-1 in metering pump A. It then exits from the pump through outlet 61 through a line as 18 and then through the upper part 52 of pinch valve 50 to mixing tee F.

The sample comes as 1 through selector valve 40 and advances through a line as 4 through the lower part 51 of the pinch valve and to the splitting tee D. The sample is then split through lines as 5, in one portion to the lower pump A, and in another portion to upper pump B. The split portion to the lower pump goes to inlet 62 of the lower piston A-2 and out the outlet 63 to a line as 6 and then to the combining tee E. The other portion of the sample goes to the lower piston B-1 of the upper pump B into inlet 64 and out outlet 65 through a line as 6 to the combining tee E. This flow pattern provides the required volume of sample to that of the reagent to maintain them in the proper ratio. The outlet to the combining tee goes through a line as 7 and through the upper part 52 of the pinch valve mechanism 50 to the mixing tee F where it is mixed with the reagent to define the reacted sample to be measured. The reacted sample comes out of the mixing tee as 8 and goes directly to the inlet 70 of the photometer 45.

The photometer 45 includes a glass cylinder 46 within which a piston 47 is received for charging and discharging a measuring cell 48 with a sample to be measured. The reacted sample in the cell is aligned with a light source 49a on one side of the cylinder and a photocell 49b on the other side of the cylinder which coact to measure the turbidity of the sample to be measured as a level of the product in the boiler feedwater. The measured sample comes out of an outlet 71 of the measuring cell and through a line as 9 to drain.

During the intake stroke of the piston 47 of the measuring cell, the final sample to be measured includes partly a new charge of the reacted sample entering the inlet 70 and partly a portion of the previously measured sample coming back from the outlet 71 and the outlet line, so the measured sample is a mixed sample, partly new and partly old. The outlet line carrying old sample as 9 is wrapped around a spool 74 several times before it is extended to drain so that there will be a sufficient volume in this drain line to prevent the leakage of air bubbles back to the measuring cell.

In order to maintain the integrity of the measuring cell, every stroke of the piston 17 cleans the glass walls of the cell to flush sediment for maintenance-free operation. Seals are provided on the piston that are continually flushed and lubricated during the operation of the analyzer. A seal flush container 75 for providing a supply of seal flush is connected into the analyzer through a line and comes in as 10. Thus, it goes out of the container as 10 through the lower part 51 of the pinch valve mechanism 50 and to the upper piston B-2 of the upper pump B. It enters the pump B through inlet 76 and is discharged through outlet 77. It goes out through a line as 11 through the upper part 52 of the pinch valve mechanism back to the upper pump B and into inlet port 78 of the upper piston B-2. It is discharged from the upper pump B through outlet port 79 to the lower pump A through a line as 16. At the lower pump the seal flush goes into the inlet port 80 of the upper piston A-1 and out the outlet port 81 as 12 and through a line to the pump C. It goes into the inlet port 82 and comes out of the outlet port 83 as 13 directly down to the measuring cell to flush the seals. It enters an inlet flushing port 84 of the measuring cell and exits through an outlet flushing port 85 as 14 and through a line to the upper part 52 of the pinch valve 50 and into the inlet port 86 of the pump C. It is discharged from the inlet port 87 as 15 and goes through a line which extends through the lower part 51 of the pinch valve mechanism to drain.

The pumps A, B and C are positive displacement pumps to meter precise amounts of solution so that the analyzer can accurately analyze the product level in the sample. It is also important that the seal flush pump C accurately pumps the seal flush solution to properly flush the seals of the measuring cells.

The metering pumps A, B and C, pinch valve 50, and positive displacement piston pump for the measuring cell are driven by a single motor in timed relation so that they operate sequentially. The pumping strokes of pumps A and B are operated simultaneously and the intake strokes of pumps A and B are operated simultaneously. Pump C is pumping when pumps A and B are on their intake strokes. When the pumps A and B are going through their pumping strokes, a lower part 51 of the pinch valve mechanism is closed to pinch and close those lines going through the lower part. During the intake stroke of pumps A and B, the upper part 52 of the pinch valve is closed and the lower part is open, respectively closing the lines going through the upper part and opening the lines going through the lower part. When the measuring cell or sample cell pump is loading the measuring cell with a sample, and therefore during the loading stroke or intake stroke, the upper part of the pinch valve is open and the lower part is closed, respectively opening the lines going through the upper part and closing the lines going through the lower part. Thereafter, during the unloading stroke of the sample cell pump, the upper part of the pinch valve is closed and the lower part is open, respectively closing the lines going through the upper part and opening the lines going through the lower part.

In order to compensate for a possible change in the light source of the measuring cell, the photocell structure includes a reference cell and a measuring cell wherein the actual measurement constitutes a difference between the signal generated in the reference cell and the signal generated in the measuring cell.

In view of the foregoing, it can be appreciated that continuous and automatic measuring of the product level which would be indicative of the level of product in the boiler feedwater system is accomplished in order to produce the optimum scale formation control so that the optimum efficiency is obtained by the boiler and downtime for cleaning scale from heat transfer surfaces is minimized.

It will be understood that modifications and variations may be effected without departing from the scope of the novel concepts of the present invention, but it is understood that this application is to be limited only by the scope of the appended claims.

The invention is hereby claimed as follows:

1. Apparatus for continuously and automatically measuring the level of a water treatment product in boiler feedwater by taking a sample from a boiler feedwater line and developing turbidity in the sample and measuring the turbidity, wherein the product includes a copolymer of acrylamide and acrylate and a copolymer of acrylic acid and sodium vinyl sulphonate and is added to the feedwater for treating hardness and scale formable on heat transfer surfaces, said apparatus comprising, a photometer comprising a measuring cell in a cylinder constructed so as to receive the sample to be photometrically measured for turbidity, said cell comprising an inlet and an outlet and a piston received in the cylinder, said piston being positioned and arranged so as to be movable in the cylinder through intake and discharge strokes, wherein the intake stroke loads the cell with a portion of the just measured reacted sample and a portion of new reacted sample, a reagent supply means containing a reagent that will only react with the total acrylate component of the product in the feedwater sample to produce a turbidity as a measure of the level of product in the feedwater, a sample inlet line for connecting to the boiler feedwater line, a reagent inlet line connected to the reagent supply means, metering pump means comprising inlets and outlets with the inlets connected to the sample and reagent inlet lines so as to provide the required volume of sample to reagent, a pinch valve having upper and lower oppositely working pinch members constructed so as to pinch lines to control flow direction in the lines, said sample and reagent inlet lines extending through one of the upper or lower pinch members of the pinch valve to said metering pump means, means for mixing the sample and reagent to form a reacted sample to be measured for turbidity, said sample and reagent inlet lines exiting from the pump means outlets and extending through the other of said upper or lower pinch members of said pinch valve to said mixing means, a reacted sample outlet line extending from the mixing means connected directly to the inlet of the measuring cell, the outlet of the cell being connected directly to a drain line, said drain line constructed so as to prevent the leakage of any air bubbles back into the cell, and means driving the pinch valve, the metering pump means, and the piston in the cylinder in timed relation, whereby the pinch valve opens the lines in the upper pinch member while closing the lines in the lower pinch member and opens the lines in the lower pinch member when closing the lines in the upper pinch member, and said driving means sequentially drives said pinch valve and said metering pump means to provide controlled flow of sample, reagent and reacted sample through the lines to the cell.

2. The apparatus of claim 1, wherein said mixing means includes a mixing tee.

3. The apparatus of claim 1, wherein said reagent is a formulation of a precipitating agent.

4. The apparatus of claim 1, wherein said driving means is constructed so that the sequence of operating the pinch valve, metering pump means and measuring cell piston is such that the lines going through the pinch valve to the mixing means are open when the measuring cell is being loaded.

5. The apparatus of claim 1, wherein the measuring cell piston is positioned and arranged so as to coact with the sample inlet to the cell and with the outlet of the cell to load the cell with reacted sample from the inlet and reacted sample from the outlet.

* * * * *